United States Patent
Wedell

(10) Patent No.: US 7,398,702 B2
(45) Date of Patent: Jul. 15, 2008

(54) AUTOMATIC SYSTEM FOR SURVEILLANCE OF COAL DUST SUPPLY TO COAL FURNACES

(75) Inventor: Anders Sten Wedell, Kvistgaard (DK)

(73) Assignee: Mark & Wedell A/S, Kvistgaard (DK)

( * ) Notice: Subject to any disclaimer, the term of this patent is extended or adjusted under 35 U.S.C. 154(b) by 0 days.

(21) Appl. No.: 10/548,701

(22) PCT Filed: Mar. 11, 2004

(86) PCT No.: PCT/DK2004/000156

§ 371 (c)(1),
(2), (4) Date: Sep. 8, 2005

(87) PCT Pub. No.: WO2004/081539

PCT Pub. Date: Sep. 23, 2004

(65) Prior Publication Data

US 2006/0207350 A1    Sep. 21, 2006

(30) Foreign Application Priority Data

Mar. 11, 2003  (DK)  ................................ 2003 00369

(51) Int. Cl.
*G01N 1/00* (2006.01)
(52) U.S. Cl. .................................................. 73/863.57
(58) Field of Classification Search ................ 73/28.01, 73/28.04, 863.03, 863.33, 863.51, 863.56, 73/863.57, 863.83, 863.82, 863.85
See application file for complete search history.

(56) References Cited

U.S. PATENT DOCUMENTS

| | | | | |
|---|---|---|---|---|
| 2,020,529 A | * | 11/1935 | Thorsten | .................. 73/863.23 |
| 2,353,828 A | * | 7/1944 | Hyde | ....................... 73/863.21 |
| 4,144,759 A | * | 3/1979 | Slowik | ..................... 73/863.21 |
| 4,442,720 A | | 4/1984 | Apley et al. | |
| 6,289,266 B1 | | 9/2001 | Payson et al. | |
| 2004/0154378 A1 | * | 8/2004 | Aguilera et al. | ............. 73/28.01 |

FOREIGN PATENT DOCUMENTS

| | | |
|---|---|---|
| DE | 3424063 | 5/1985 |
| EP | 1413873 | 4/2004 |
| WO | WO 98/10266 | 3/1998 |
| WO | WO 02/095364 | 11/2002 |

* cited by examiner

*Primary Examiner*—Robert R Raevis
(74) *Attorney, Agent, or Firm*—James Creighton Wray; Clifford D. Hyra

(57) ABSTRACT

A method is provided for surveillance and balancing of coal dust supply through channels to coal furnaces. Data is gathered from results of automatic sample collections of coal dust particles conveyed by air current in circular channels from a coal crusher to a coal furnace. Data is processed for generating control parameters for a cross-section area regulating draught control unit in each of the respective channels. Each control parameter is adapted to control a respective draught control unit to change cross-section of the channel in size and direction for reducing differences in coal dust conveyance of channels. A completely or practically constant surveillance and balancing of coal dust supply in two or more channels to a coal furnace can be made automatically, resulting in reduced emission and/or improved fuel economy. A collector and a draught control unit apparatus for carrying out the method is also provided.

17 Claims, 2 Drawing Sheets

# AUTOMATIC SYSTEM FOR SURVEILLANCE OF COAL DUST SUPPLY TO COAL FURNACES

This application claims the benefit of Danish Application No. PA 2003 00369 filed Mar. 11, 2003 and PCT/DK2004/000156 filed Mar. 11, 2004, which are hereby incorporated by reference in their entirety.

BACKGROUND OF THE INVENTION

The present invention relates to a method of the kind mentioned in the introductory clause of claim 1 for surveillance and balancing of coal dust supply to coal furnaces, and a collector and a cross section regulating draught control unit for carrying out the method.

Until now such method has not been carried out all-automatically but has been the object of comprehensive research with no practically realizable results.

A collector and its associated sample collecting apparatus are known from Danish patent No. 172643, U.S. Pat. No. 4,479,393 and U.S. Pat. No. 4,442,720. However, it is not suitable for a constant surveillance and automatic control of the coal dust supply.

SUMMARY OF THE INVENTION

It is the purpose of the present invention to provide a method of the kind mentioned above, whereby the samples can be collected in a well known way as well as in accordance with ISO 9931 or the like, and a constant or practically constant surveillance and balancing of the coal dust supply in two or more conveying pipes to a coal furnace can be made automatically with a consequently reduced emission and/or improved fuel economy.

This is achieved by a method of the kind mentioned above, which method according to the invention is characterized by the measures stated in the characterizing clause of claim 1.

By the subject matter of claim 2 a preferred embodiment for the sample collection is achieved.

By the subject matter of claim 3 is achieved a preferred starting arrangement causing the smallest possible reduction of the cross section area of the channels in operation but will nevertheless allow said balancing of the coal dust supply in the tubes.

By the collector according to the introductory part of claim 4 is achieved by the characterizing clause a substantial simplification of the collector with suction orifices without provable change of the sample collection results obtained.

By the subject matter of claim 5 is achieved an intentional increase of the periods of time between the necessary replacements of the parts comprising the collector, the common tube and the screen plate.

By the subject matter of claim 6 a further service improvement is achieved, as said mounting unit can be removed and inserted in the channel with no need of interrupting the coal dust supply therein. This is due to the fact that said coal dustless connection with its air carpet control gate prevents a coal dust flow during and between the removing and inserting operations.

By the subject matter of claim 7 is achieved a cross section regulating draught control unit which in a simple way contributes to the coal dust conveyance balancing function according to the invention between more channels, since each tube is provided with such draught control unit controlled by the sample collection and the data processor.

The subject matter of claim 8 defines preferred embodiments of this cross section area regulating draught control unit draught control plates.

The invention will now be described in more detail with reference to the drawings in which

Figure 1:
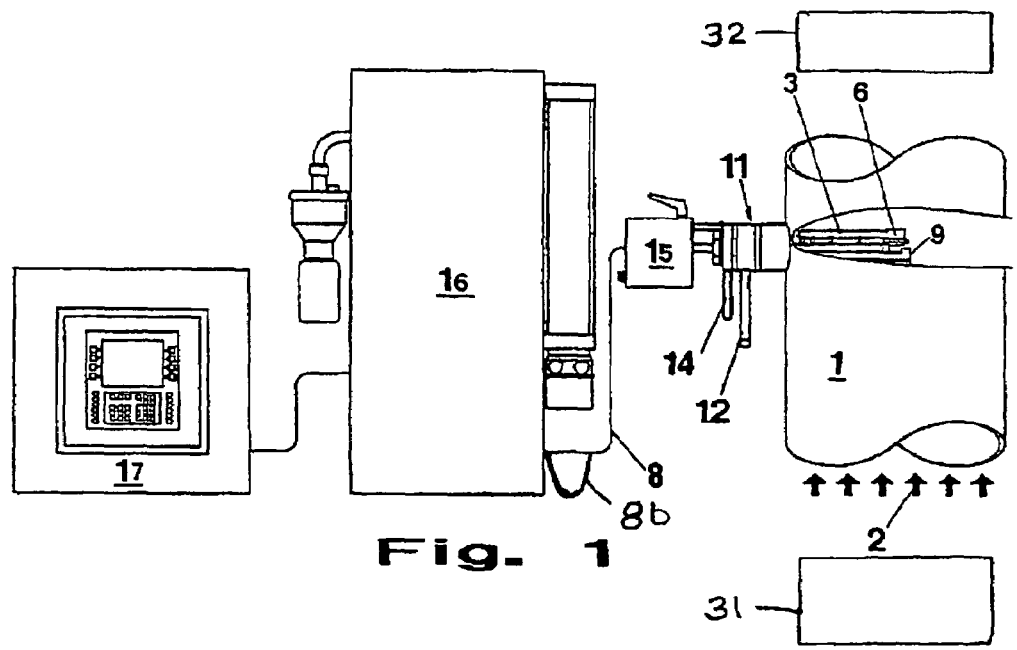
FIG. 1 shows a plant for sample collection of coal dust from a channel to a coal furnace, said plant consisting of a collector, a dustless connection, a unit of measurement, and a data processor.

A channel 1 for coal dust airborne in the arrow direction 2 for the burner (not shown) of a coal furnace is provided with a collector 3 with suction orifices 4 for the collection or sample collection of coal dust from the channel 1. A right-angle gear 6 for rotation of the collector 3 is mounted centrally in the tube on the innermost end of a common tube 7 for conveying a drive unit for driving the right angle gear 6 and for connection of a suction orifice 4 via the right angle gear 6 to the collector 3. Upstream the common tube 7 is arranged a screen plate 9 as wear part for the protection of the common tube and the collector in the position shown, viz. the inactive position between sample collection cycles.

DETAILED DESCRIPTION OF THE PREFERRED EMBODIMENTS

The collector 3, the common tube 7 and the possible screen plate 9 form a mounting unit which in full goes in through and is secured in a so called dustless connection 11 fastened in the conveyor tube wall. Said connection has an air carpet control gate, a compressed air supply 12 and a handle part 14 for a plug. Thus, the suction channel 8 and the drive unit for the right-angle gear 6 also go through the connection 11 and out to a electric power supplied drive mechanism 15 for the right-angle gear 6. From there the suction channel 8 continues to a weighing and measuring unit 16 in which a data signal significant for the flow in the conveyor tube is generated.

Said signal is transmitted to a data processor 17 for processing, and based thereon said processor is determining a control signal in case the flow in the channel should be altered. If so, said signal is sent to a draught control unit 18, cf FIGS. 5A and 5B, for altering the amount of coal dust of the channel 1 by altering the free passage area in the tube.

Figure 2:
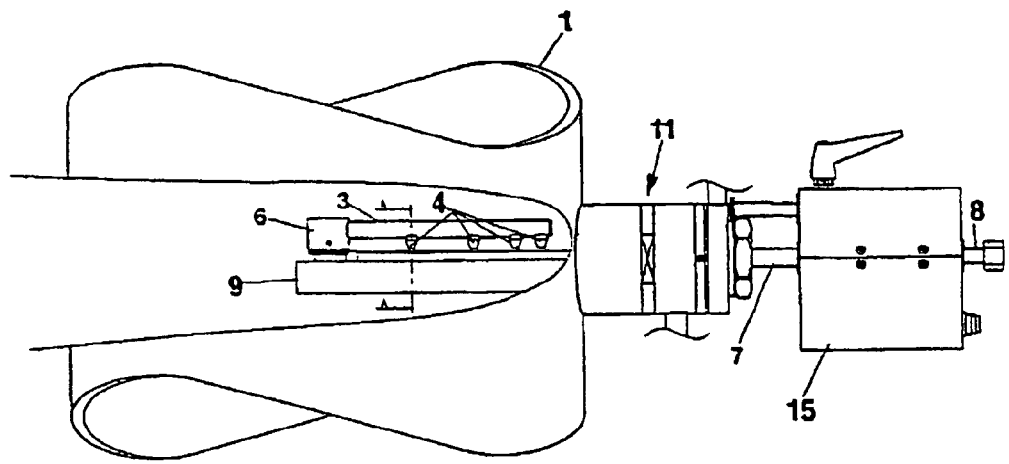
FIG. 2 is a collector and a dustless connection mounted on a coal dust channel shown at a larger scale.
Figure 3:
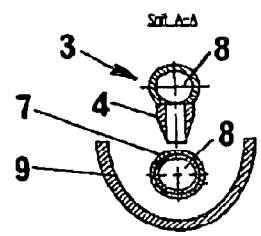
FIG. 3 is a section A-A in FIG. 2 of the common tube, the collector and the screen plate at a larger scale.

FIGS. 2-3 show a common tube, collector and screen plate at a larger scale, and section A-A of FIG. 2 shows how the plate 9 in the inactive position of the collector 3 protects the common tube 7 and the collector against wear caused by the coal dust particles.

Figure 4:
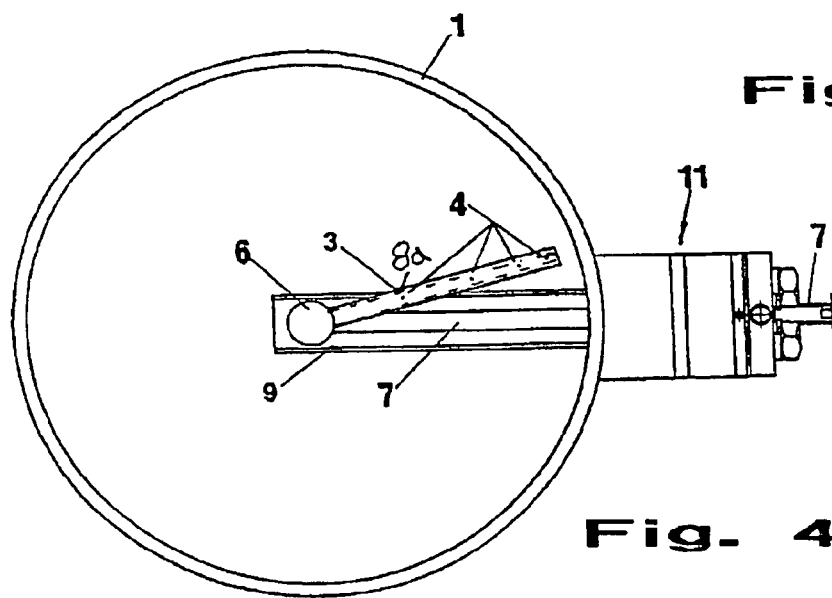
FIG. 4 is a top view of the left part of FIG. 2, and FIG. 5A and 5B show a plan view and a side view, respectively, of a draught control unit.

FIG. 4 shows the collector 3 turned slightly out from its inactive position.

Figures 5A, 5B:
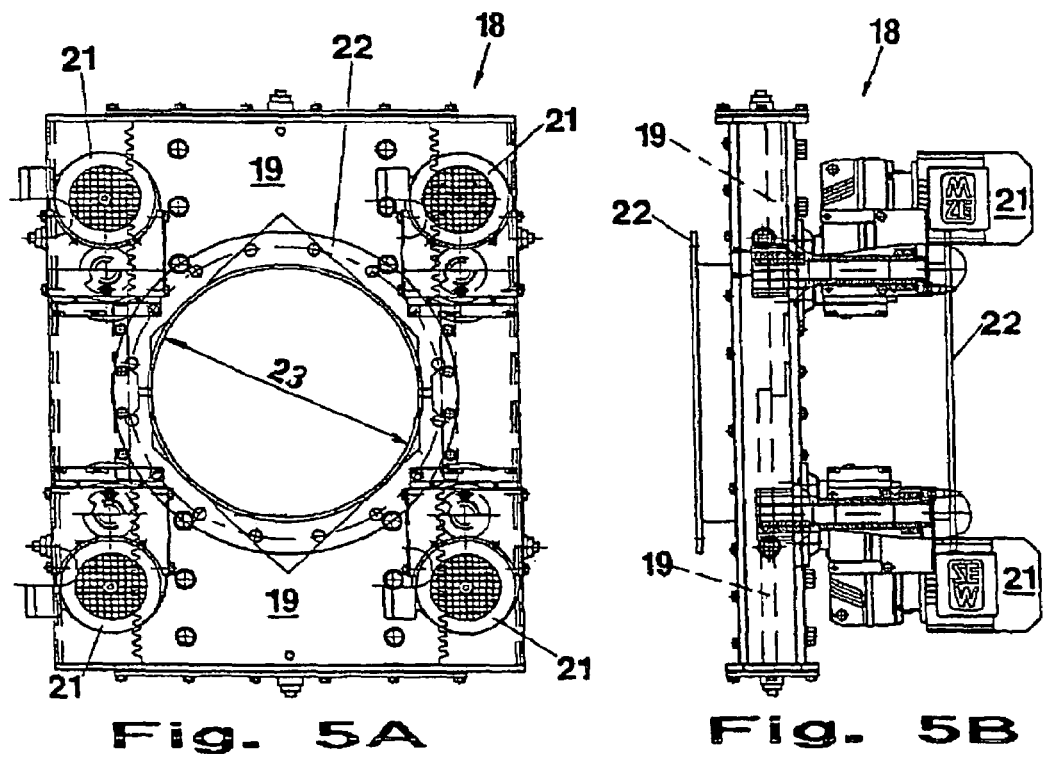

FIGS. 5A and 5B show a cross section area regulating draught control unit 18 mounted on a short channel part with flange connections 22, said unit 18 comprising two draught control plates 19, each of which is operated by two draught control motors 21 synchronized by the draught control plates. The conveyor tube part has a slightly larger or the same nominal diameter 23 as the conveyor tube in which the draught control unit 18 has been mounted.

The coal dust particles are conveyed by air currents 2 in circular conveyor channels 1 from a coal crusher 31 to a coal furnace 32.

The suction channels 8 of the collector 3 are mutually integrated with no mutual partition walls inside an individual suction tube 8 extending from the outermost collecting orifice 4 to the mechanical transmission 6 and preferably has an inner cross section 8a increasing in the direction away from the outermost orifice 4.

A collected sample of air with coal dust particles leads via the suction channels 8 and further through a common tube 7 leading out through an opening in the conveyor channel 1 to a cyclone 8b which may segregate the coal dust particles.

The invention claimed is:

1. Draught control unit (18) in a collector for an apparatus for the sample collection of coal dust particles being conveyed by an air current in a circular conveyor channel (1) from a coal crusher to a coal furnace, said collector (3) having unequally long distances in inner suction channels (8) extending in the collector's longitudinal direction, which suction channels (8), when the collector (3), which has been entered in the conveyor channel (1), can be caused to rotate about the axis of the channel (1) in a plane perpendicularly to the axis by a mechanical transmission, said suction channels (8) at their ends each are connected to a different suction orifice (4) with an aperture directed towards the air current in the conveyor channel (1) and which can lead a collected sample of air with coal dust particles via the suction channels (8) and further through a common tube (7) leading out through an opening in the conveyor channel (1) to a cyclone which may segregate the coal dust particles and lead them to a sample receptacle for the purpose of determining the quantity of coal dust conveyed, and where the respective orifices (4) are unequally long distances from the axis of rotation, characterized in that the collector (3) is in an inactive position between sample cycles and that a screen plate (9) is mounted upstream the common tube to protect the common tube (7) and the collector against wear caused by the coal dust particles thereby increasing the periods of time between the necessary replacements of the parts comprising the collector, the common tube and the screen plate, wherein the collector (3) is provided for effecting said sample collections and wherein the screen plate (9) is provided to protect said collector (3) and said common tube (7) against wear caused by the coal dust particles, said draught control unit (18) is of the draught control plate type for altering the cross section of a coal dust supply channel (1) with such size and in such a direction that possible differences in the coal dust conveyance of channels (1) is completely or partly reduced, characterized in that it comprises two draught control plates (19) being oppositely and symmetrically synchronously displaceable around a tube axis, whereby said plates (19) in the mounted condition of the draught control unit (18) are arranged perpendicularly to the axis of the tube, and each of which is operated by two synchronously driven motors (21) being adapted to receive control parameters from a data processor (17), and to occupy a rotating direction determined thereby during a period of rotation likewise determined thereby, and that both draught control plates (19) thus are synchronously displaceable between an outermost position in which they provide the channel (1) with a largest flow cross section, and an innermost position in which they provide the channel (1) with its smallest flow cross section.

2. Draught control unit according to claim 1, characterized in that the space between the two draught control plates (19) forms a symmetrical flow area which can be regulated around the tube axis, and that the motors (21) are gear motors each with a gear wheel on the outgoing axis, each gear wheel engaging an opposite corresponding toothed edge on a draught control plate (19).

3. The draught control unit of claim 2, wherein the symmetrical flow area is practically square with rounded corners.

4. The draught control unit of claim 2, wherein the symmetrical flow area is partly circular.

5. The draught control unit of claim 1, wherein the suction channels (8) of the collector are mutually integrated with no partition walls such that they constitute only paths, and not physical conduits, inside an individual suction tube (8) extending from the outermost collecting orifice (4) to the mechanical transmission (6) and having an inner cross section (8a) increasing in the direction away from the outermost orifice (4).

6. The draught control unit of claim 1, wherein the mechanical transmission is a right-angle gear.

7. The draught control unit of claim 1, wherein the suction orifices further comprise nozzles.

8. Collector for an apparatus for the sample collection of coal dust particles being conveyed by an air current in a circular conveyor channel (1) from a coal crusher to a coal furnace, said collector (3) having unequally long distances in inner suction channels (8) extending in the collectors longitudinal direction, which suction channels (8), when the collector (3), which has been entered in the conveyor channel (1), can be caused to rotate about the axis of the channel (1) in a plane perpendicularly to the axis by a mechanical transmission, said suction channels (8) at their ends each are connected to a different suction orifice (4) with an aperture directed towards the air current in the conveyor channel (1) and which can lead a collected sample of air with coal dust particles via the suction channels (8) and further through a common tube (7) leading out through an opening in the conveyor channel (1) to a cyclone which may segregate the coal dust particles and lead them to a sample receptacle for the purpose of determining the quantity of coal dust conveyed, and where the respective orifices (4) are unequally long distances from the axis of rotation, characterized in that the collector (3) is in an inactive position between sample cycles and that a screen plate (9) is mounted upstream the common tube to protect the common tube (7) and the collector against wear caused by the coal dust particles thereby increasing the periods of time between the necessary replacements of the parts comprising the collector, the common tube and the screen plate, wherein its parts, the common tube (7) and the screen plate (9), are made from a material which is wear proof to coal dust, wherein the material is metal covered with a wear layer or protective layer.

9. Collector according to claim 8, characterized in that the suction channels (8) of the collector are mutually integrated with no partition walls such that they constitute only paths, and not physical conduits, inside an individual suction tube (8) extending from the outermost collecting orifice (4) to the mechanical transmission (6) and having an inner cross section (8a) increasing in the direction away from the outermost orifice (4).

10. The collector of claim 8, wherein the mechanical transmission is a right-angle gear.

11. The collector of claim 8, wherein the material is steel.

12. The collector of claim 8, wherein the wear layer or protective layer comprises titanium dioxide.

13. The collector of claim 8, wherein the wear layer or protective layer comprises synthetic rubber.

14. The method of claim 8, wherein the suction orifices further comprise nozzles.

15. Method for the surveillance and balancing of the coal dust supply through circular conveyor channels (1) to coal furnaces wherein a data processing (17) is carried out on the basis of results of automatic sample collections, made by collectors (3), of coal dust particles conveyed by air currents (2) in the circular conveyor channels (1) from a coal crusher to one of the coal furnaces, comprising processing said data and generating control parameters for a cross section area regulating draught control unit (18) in each of the respective conveyor channels (1), adapting each of said control parameters to control the respective draught control unit (18) for altering the cross section of the corresponding conveyor channel (1) with such size and in such a direction that possible differences in the coal dust conveyance of the channels are completely or partly reduced, effecting said sample collections by one of the collectors (3) having unequally long distances of inner suction channels (8) extending in the collector's longitudinal direction, which suction channels (8), when the collector (3), which has been entered in the conveyor channel (1), are caused to rotate about an axis of the conveyor channel (1) in a plane perpendicularly to the axis by a mechanical transmission, wherein the one collector (3) is in an inactive position between sample cycles, leading a collected sample of air with coal dust particles via the suction channels (8) and further through a common tube (7) leading out through an opening in the conveyor channel (1), and wherein a screen plate (9) is mounted upstream the common tube to protect the common tube (7) and the collector against wear caused by the coal dust particles thereby increasing the periods of time between the necessary replacements of the parts comprising the collector, the common tube and the screen plate, wherein the adapting said control parameters further comprises completely opening the draught control unit with lowest flow and allowing it to act as master and balancing the remaining draught control units accordingly.

16. The method of claim 15, wherein the mechanical transmission is a right-angle gear.

17. Collector for an apparatus for the sample collection of coal dust particles being conveyed by an air current in a circular conveyor channel (1) from a coal crusher to a coal furnace, said collector (3) having unequally long distances in inner suction channels (8) extending in the collector's longitudinal direction, which suction channels (8), when the collector (3), which has been entered in the conveyor channel (1), can be caused to rotate about the axis of the channel (1) in a plane perpendicularly to the axis by a mechanical transmission, said suction channels (8) at their ends each are connected to a different suction orifice (4) with an aperture directed towards the air current in the conveyor channel (1) and which can lead a collected sample of air with coal dust particles via the suction channels (8) and further through a common tube (7) leading out through an opening in the conveyor channel (1) to a cyclone which may segregate the coal dust particles and lead them to a sample receptacle for the purpose of determining the quantity of coal dust conveyed, and where the respective orifices (4) are unequally long distances from the axis of rotation, characterized in that the collector (3) is in an inactive position between sample cycles and that a screen plate (9) is mounted upstream the common tube to protect the common tube (7) and the collector against wear caused, by the coal dust particles thereby increasing the periods of time between the necessary replacements of the parts comprising the collector, the common tube and the screen plate, wherein the collector, common tube, and screen plate together are an entire removable and replaceable mounting unit, further comprising a dust reducing connection fastened in the conveyer tube wall comprising an air control gate, wherein the mounting unit goes into the conveyer tube through the dustless connection and is mounted therein, and the air control gate prevents dust flow during and between removing and inserting the mounting unit, whereby the mounting unit can be removed and inserted without interrupting the coal dust supply.

\* \* \* \* \*